(12) United States Patent
Takase et al.

(10) Patent No.: US 7,794,397 B2
(45) Date of Patent: Sep. 14, 2010

(54) ENDOSCOPE HAVING AN ILLUMINATION LENS SUBJECTED TO LIGHT DIFFUSION PROCESS

(75) Inventors: Seisuke Takase, Tokyo (JP); Masaaki Miyagi, Tokyo (JP); Hiroki Moriyama, Tokyo (JP)

(73) Assignee: Olympus Corporation, Tokyo (JP)

( * ) Notice: Subject to any disclaimer, the term of this patent is extended or adjusted under 35 U.S.C. 154(b) by 1096 days.

(21) Appl. No.: 11/453,108

(22) Filed: Jun. 14, 2006

(65) Prior Publication Data

US 2006/0235276 A1  Oct. 19, 2006

Related U.S. Application Data

(63) Continuation of application No. PCT/JP2004/018740, filed on Dec. 15, 2004.

(30) Foreign Application Priority Data

Dec. 17, 2003  (JP) .............................. 2003-420093

(51) Int. Cl.
*A61B 1/07* (2006.01)
(52) U.S. Cl. ........................ 600/182; 600/176; 600/177; 600/129
(58) Field of Classification Search .................. 600/182, 600/176, 177, 129
See application file for complete search history.

(56) References Cited

U.S. PATENT DOCUMENTS

| | | | | |
|---|---|---|---|---|
| 4,403,273 A | * | 9/1983 | Nishioka | ..................... 362/574 |
| 4,610,513 A | * | 9/1986 | Nishioka et al. | ............... 385/33 |
| 4,671,630 A | * | 6/1987 | Takahashi | ..................... 359/503 |
| 4,929,070 A | * | 5/1990 | Yokota et al. | ................ 600/177 |
| 5,305,736 A | * | 4/1994 | Ito | ............................. 600/109 |
| 5,871,440 A | * | 2/1999 | Okada | ......................... 600/129 |
| 5,980,454 A | * | 11/1999 | Broome | ...................... 600/176 |
| 6,503,196 B1 | * | 1/2003 | Kehr et al. | .................... 600/176 |
| 6,569,088 B2 | * | 5/2003 | Koshikawa | .................. 600/177 |
| 7,324,292 B2 | * | 1/2008 | Takasugi | ..................... 359/707 |
| 7,585,274 B2 | * | 9/2009 | Homma | ....................... 600/160 |
| 2005/0272979 A1 | * | 12/2005 | Pauker et al. | ................ 600/173 |
| 2006/0052668 A1 | * | 3/2006 | Homma | ....................... 600/177 |
| 2006/0217592 A1 | * | 9/2006 | Miyagi et al. | ................ 600/130 |

FOREIGN PATENT DOCUMENTS

| | | |
|---|---|---|
| JP | 10-99268 | 4/1998 |
| JP | 2000-193894 | 7/2000 |
| JP | 2001-258823 | 9/2001 |

* cited by examiner

*Primary Examiner*—John P Leubecker
(74) *Attorney, Agent, or Firm*—Scully, Scott, Murphy & Presser, P.C.

(57) ABSTRACT

An endoscope includes an insertion unit; an observation optical system arranged at an end surface of the insertion unit in an inserting axis direction and having a wide viewing angle for observing a body cavity; and a plurality of illumination optical systems arranged on an axis slanted with respect to the inserting axis direction of the insertion unit and used when illuminating the body cavity. An illumination lens of at least one of the illumination optical systems is subjected to light diffusion process.

10 Claims, 5 Drawing Sheets

ENDOSCOPE HAVING AN ILLUMINATION LENS SUBJECTED TO LIGHT DIFFUSION PROCESS

CROSS-REFERENCE TO RELATED APPLICATIONS

This application is a continuation of PCT international application Ser. No. PCT/JP2004/018740 filed Dec. 15, 2004 which designates the United States, incorporated herein by reference, and which claims the benefit of priority from Japanese Patent Applications No. 2003-420093, filed Dec. 17, 2003, incorporated herein by reference.

BACKGROUND OF THE INVENTION

1. Field of the Invention

The present invention relates to endoscopes, more, specifically, to a wide angle endoscope in which an observation optical system has a wide viewing angle.

2. Description of the Related Art

As well known in the art, endoscopes have been widely used in the medical field and the like. The endoscope is able to observe the organs inside the body cavity by inserting an elongated insertion unit into the body cavity, or to perform various treatments using a treatment instrument inserted into an insert channel for the treatment instrument as necessary.

A bendable part is arranged at the distal end of the insertion unit, and the observing direction of an objective lens at the end of the observation optical system arranged in the insertion unit can be changed by operating the operating unit of the endoscope to bend the bendable part.

The viewing angle of the observation optical system of the conventional endoscope is about 140°, for example, and the operator observes the body cavity with the observation image of the relevant viewing angle, but when desiring to observe a region outside the field of view, the operator bends the bendable part to observe the region outside the field of view, as described above.

However, when observing the inside of the large intestine and the like, the desired observation image of the back side of the lamella of the large intestine and the like cannot be obtained by simply bending the bendable part. In view of such situation, an endoscope having a wider viewing angle to allow the observation of a wider range is proposed (see e.g., Japanese Patent Application Laid-Open (JP-A) No. 2001-258823).

The endoscope proposed in Patent Document 1 has the observation optical system having a wide viewing angle, e.g., 180° arranged at the bendable part and the distal end portion of the insertion unit. Further, when the observation optical system is made to have a wider angle, an illumination optical system, arranged at the bendable part and the distal end portion of the insertion unit and illuminating the body cavity, is arranged on an axis slanted with respect to an axis direction where the observation optical system is arranged for even and thorough illumination of the body cavity.

Further, the illumination optical system illuminates the observing range of wide angle of the observation optical system with a sufficient brightness and light distribution, and thus is generally configured with a plurality of illumination lenses (see e.g., JP-A No. 10-99268).

SUMMARY OF THE INVENTION

An endoscope according to one aspect of the present invention includes an insertion unit; an observation optical system arranged at an end surface of the insertion unit in an inserting axis direction and having a wide viewing angle for observing a body cavity; and a plurality of illumination optical systems arranged on an axis slanted with respect to the inserting axis direction of the insertion unit and used when illuminating the body cavity. An illumination lens of at least one of the illumination optical systems is subjected to light diffusion process.

An endoscope according to another aspect of the present invention includes an insertion unit; an observation optical system arranged in an inserting axis direction of the insertion unit and used when observing a body cavity having a wide viewing angle; at least one illumination optical system arranged at an end surface of an axis slanted with respect to the inserting axis direction of the insertion unit and used when illuminating the body cavity; an optical fiber bundle connected to a back end of at least one illumination lens, and including a rigid portion at a front in the inserting axis direction and a soft portion at a back in the inserting axis direction; and a rigid part, arranged at the insertion unit, for grasping the optical fiber bundle. A back end of the rigid portion of the optical fiber bundle is arranged on a proximal end side than a back end face of the rigid part in the inserting axis direction.

The above and other objects, features, advantages and technical and industrial-significance of this invention will be better understood by reading the following detailed description of presently preferred embodiments of the invention, when considered in connection with the accompanying drawings.

DETAILED DESCRIPTION OF THE PREFERRED EMBODIMENTS

The embodiments of the present invention will now be described with reference to the drawings.

Figure 1:
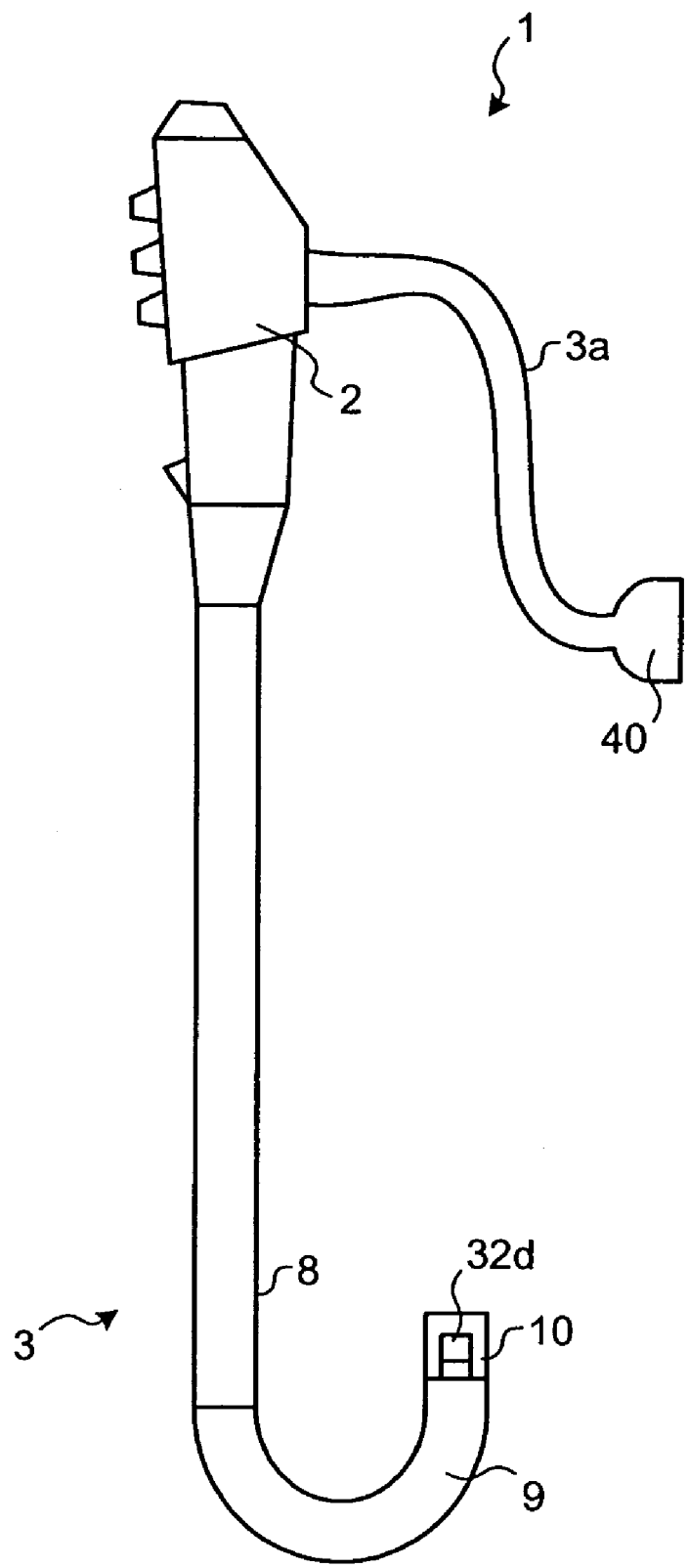
FIG. 1 is a front view schematically showing an endoscope of one embodiment according to the present invention.

FIG. 1 is a front view schematically showing an endoscope of one embodiment of the present invention.

As shown in FIG. 1, the endoscope 1 includes an operating unit 2 for performing bending operation and control of the channel system, an insertion unit 3 having a proximal end connected to the operating unit 2 and being inserted into the body cavity, and a universal cable 3a extended from the operating unit 2 and including a connector unit 40 at its end. The connector unit 40 is connected to a light source and the like (not shown) by way of a predetermined connector.

A flexible tube 8, a bendable part 9 arranged at the distal end side of the tube 8, and a distal end portion 10 arranged on the distal end side of the bendable part 9 are arranged in the insertion unit 3. An imaging element 32d for imaging a region in the body cavity is embedded in the distal end portion 10.

A bending operation knob for remotely bending the bendable part 9 is arranged at the operating unit 2. An operation wire (not shown) inserted into the insertion unit 3 is pulled and released by operating the operation knob, and as a result, the bendable part 9 can be bent in four directions.

Figure 2:
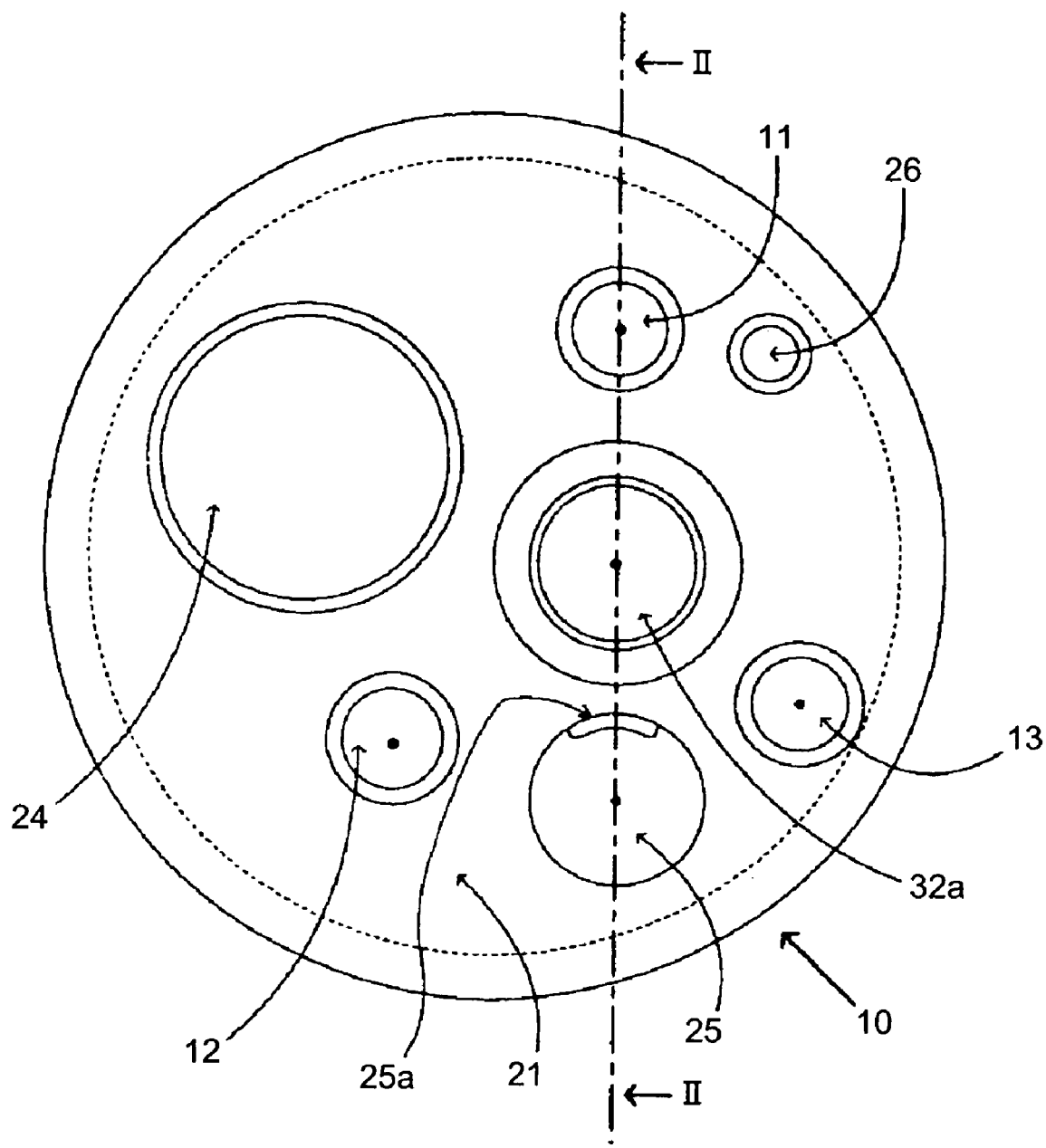
FIG. 2 is a front view of an end surface of an insertion unit of the endoscope of FIG. 1.

FIG. 2 is a front view of an end surface of the insertion unit of the endoscope of FIG. 1.

As shown in FIG. 2, the end surface 21 of the distal end portion 10 of the endoscope insertion unit 3 is arranged with an objective lens 32a, three illumination lenses 11, 12, and 13 which are an illumination optical system and the like, a treatment instrument opening 24, an air and water feeding nozzle 25 for washing the dirt on the objective lens 32a or the three illumination lenses 11, 12, and 13 by feeding air or water when inserting the distal end portion 10 into the body cavity, and a forward water feeding nozzle 26 for washing blood, mucus and the like from the affected area of the body cavity. Therefore, the end surface 21 of the distal end portion 10 is arranged with a plurality of openings for arranging the objective lens 32a, the three illumination lenses 11, 12, and 13, the treatment instrument opening 24, the air and water feeding nozzle 25, and the forward water feeding nozzle 26.

The three illumination lenses 11, 12, and 13 are arranged in the vicinity of the peripheral edge of the objective lens 32a at an interval of a predetermined angle. Further, the treatment instrument opening 24, the air and water feeding nozzle 25, and the forward water feeding nozzle 26 are arranged between adjacent illumination lenses and in the vicinity of the peripheral edge of the objective lens 32a.

Specifically, the treatment instrument opening 24 is arranged between the illumination lens 11 and the illumination lens 12, the air and water feeding nozzle 25 is arranged between the illumination lens 12 and the illumination lens 13, and the forward water feeding nozzle 26 is arranged between the illumination lens 13 and the illumination 11.

Figure 3:
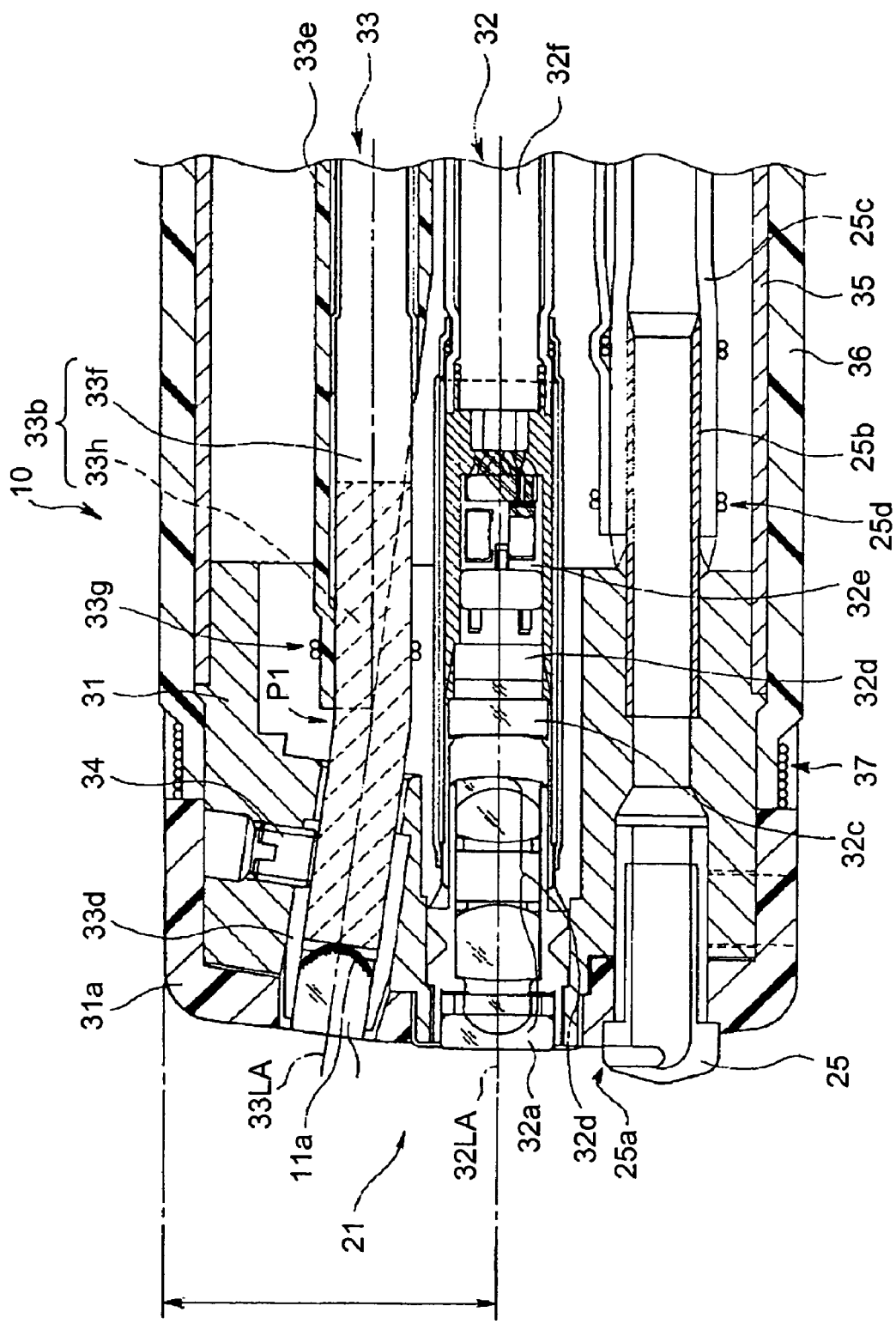
FIG. 3 is a longitudinal,cross-sectional view taken along line II-II of the endoscope of FIG. 2.
Figure 4:
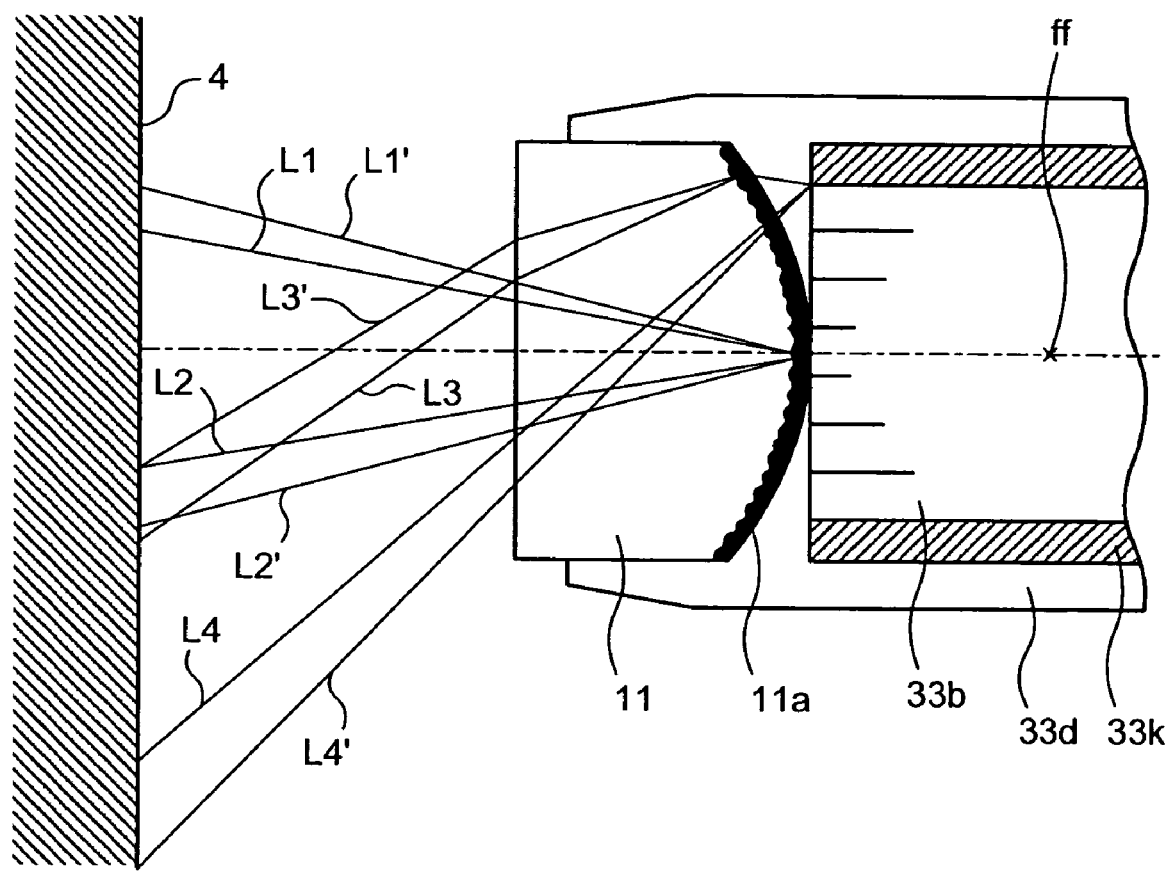
FIG. 4 is an enlarged front view of an illumination lens of FIG. 3.

FIG. 3 is a longitudinal cross-sectional view taken along line II-II of the endoscope of FIG. 2, and FIG. 4 is an enlarged front view of the illumination lens of FIG. 3.

As shown in FIG. 3, a distal end rigid portion 31 including a space for arranging an imaging unit 32 arranged parallel to the axis at where the distal end portion 10 is inserted, a light guide unit 33 for exiting light to the illumination lens 11 and the like is arranged inside the distal end portion 10. A cap 31a for covering the front surface and the outer peripheral surface of the distal end rigid portion 31 is placed on the distal end side in the axis direction of inserting the distal end rigid portion 31.

The imaging unit 32 is inserted and fixed to the distal end rigid portion 31. The imaging unit 32 includes observation optical system 32b configured with a plurality of lenses having a wide viewing angle including the objective lens 32a having a wide viewing angle of greater than or equal to 150°, for example, between 150° to 170°, a cover glass 32c arranged on the back end side of the observation optical system 32b, and an imaging element 32d, which is a solid-state imaging device such as CCD arranged on the back end side of the cover glass 32c.

The imaging unit 32 further includes a substrate 32e that is connected to the imaging element 32d and that includes various circuits. A signal cable 32f is connected to the substrate 32e. The signal cable 32f is inserted through the insertion unit 3 and connected to a video processor (not shown) connected with the endoscope. The imaging unit 32 is fixed to the distal end rigid portion 31 with a filling material and the like (not shown).

The light guide unit 33 has a main part configured with the illumination lens 11 of at least one illumination optical system, and an optical fiber bundle 33b is constituted of a plurality of optical fibers which are light guides arranged on the back. end side of the illumination lens 11.

The end of a rigid portion 33h of the optical fiber bundle 33b and the illumination lens 11 are inserted and fixed to a frame 33d. The exit end face of the optical fiber bundle 33b and the illumination lens 11 are arranged directly adjacent to each other, as shown in FIG. 3. Thus, the length in the inserting axis direction of the distal end rigid portion 31 itself is made shorter.

The light guide unit 33 is fixed to the distal end rigid portion 31 with a fixation screw 34. The light guide unit 33 is further extended backwards from the distal end rigid portion 31 and connected to the illumination device (not shown).

The end of the rigid portion 33h of the optical fiber bundle 33b may be fixed to the frame 33d by way of a mouthpiece 33k configured with a pipe and the like, as shown in FIG. 4. Specifically, the mouthpiece 33k is attached to the outer periphery of the end of the rigid portion 33h of the optical fiber bundle 33b, and the mouthpiece member 33 is fitted to and fixed to the inner periphery of the frame 33d.

When fixing the optical fiber bundle 33b to the frame 33d, the positional shift between the optical fiber bundle 33b and an optical axis 32LA in assembling is prevented by using the mouthpiece 33k, and the precision and balance efficiency of the diffusion of light emitted from the illumination lens 11 when the optical fiber bundle 33b and the illumination lens 11 are combined are enhanced.

That is, when assembling the illumination lens 11 and the optical fiber bundle 33b directly to the distal end rigid portion 31 without using the mouthpiece 33k and the frame 33d, the precision of diffusion of the light emitted from the illumination lens 11 when the optical fiber bundle 33b and the illumination lens 11 are combined depends on the processing precision of the distal end rigid portion 31 and the illumination lens 11 or the outer diameter precision of the optical fiber bundle 33b, but such problem is solved by fitting the mouthpiece 33k to the frame 33d and arranging the illumination lens 11 to the distal end rigid portion 31.

Further, when using the mouthpiece 33k and the frame 33d, the frame 33d is first attached to the distal end rigid portion 31 and thereafter, the mouthpiece 33k attached to the optical fiber bundle 33b is inserted and fitted to the distal end rigid portion 31 in assembling.

Although the insert and fitting task is difficult to perform since the optical fiber bundle is soft when inserting and fitting the optical fiber bundle not attached to the mouthpiece 33k to the distal end rigid portion 31, the assembly task can be enhanced by the above configuration.

Referring back to FIG. 3, the optical fiber bundle 33b is covered by an envelope tube 33e. The envelope tube 33e is fixed to the outer periphery of the optical fiber bundle 33b with a reel 33g.

The optical fiber bundle 33b is bent at a predetermined position P1 in the middle. Therefore, the optical axis 33LA of the illumination lens 11 for emitting the illumination light is not parallel to the optical axis 32LA of the imaging unit 32. That is, the optical axis 33LA is slanted with respect to the optical axis 32LA in a direction the distal end direction of the optical axis 33LA moves away from the previous point in the observing direction of the optical axis 32LA of the imaging unit 32.

The optical axis of the light guide unit 33 corresponding to the other illumination lenses 12 and 13 is also slanted with respect to the optical axis 32LA in a direction the distal end direction of the optical axis moves away from the previous point in the observing direction of the optical axis 32LA of the imaging unit 32. Thus, the distal end side of the light guide unit 33 is arranged slanted with respect to the observation optical system 32b, and the surface of the illumination lens 11 is arranged slanted with respect to the surface of the objective lens 32a.

Since the objective lens 32a and the observation optical system 32b are configured with a lens having a wide viewing angle, the light guide unit 33 illuminating the body cavity must evenly and thoroughly irradiate the body cavity.

Since the light guide unit 33 is arranged slanted with respect to the observation optical system 32b, the rigid portion 33h is formed on the optical fiber bundle 33b by being secured with an adhesive and the like to enhance insertability when inserting the optical fiber bundle 33b into the distal end rigid portion 31 in assembling. Thus, the optical fiber bundle 33b is configured by the rigid portion 33h and a soft portion 33f formed by bonding the bundle of a plurality of optical fibers.

The rigid portion 33h is formed at the front in the inserting axial direction of the optical fiber bundle 33b, and the soft portion 33f is formed at the back in the inserting axial direction of the optical fiber bundle 33b. The optical fiber bundle 33b is held by the distal end rigid portion 31 so that the interface of the rigid portion 33h and the soft portion 33f, that is, the back end of the rigid portion 33h is positioned towards the proximal end side than the back end face of the distal end rigid portion 31 in the inserting axial direction.

This is because although the optical fiber bundle 33b is inserted to a defined space of the distal end rigid portion 31 as the operator grasps and pushes the optical fiber bundle 33b, if the rigid portion 33h is formed so that the interface of the rigid portion 33h and the soft portion 33f is positioned toward the distal end side than the back end face in the distal end rigid portion 31, the operator must grasp the soft portion 33f, whereby the pushing force becomes difficult to be conveyed to the distal end portion of the optical fiber bundle 33b and the assembly efficiency becomes unsatisfactory.

As described above, if the interface is arranged on the proximal end side than the back end face of the distal end rigid portion 31 in the inserting axial direction, the operator is able to grasp the rigid portion 33h and insert the optical fiber bundle 33b to the space of the distal end rigid portion 31, and thus the pushing force is reliably conveyed to the end of the optical fiber bundle 33b, thereby enhancing the assembling ability.

Further, the illumination lens 11 is configured with one lens performed with light diffusion process. Specifically, as shown in FIG. 4, the illumination lens 11 is formed by one convex lens, and the light diffusion surface 11a is formed on at least one surface excluding the surface facing the observing site in the body cavity, for example, a curvature surface contacting the exit end face of the optical fiber bundle 33b.

If the light diffusing surface 11a is not formed on the illumination lens 11, the light ray emitted from the exit end face of the optical fiber bundle 33b does not image but converges as in L1, L2, L3, and L4. In other words, the light distribution unevenness of mesh shape in which the mesh pattern of the exit end face of the optical fiber bundle 33b is imaged on the imaging surface 4 occurs at the imaging surface 4.

Further, when actually assembling the light guide unit 33, a space is formed between the exit end face of the optical fiber bundle 33b and the illumination lens 11 due to interference and the like with the other members constituting the observation optical system 32b and the like. When this occurs, the exit end face of the optical fiber bundle 33b approaches the back focal position ff of the illumination lens 11, the mesh pattern of the exit end face of the optical fiber bundle 33b images on the imaging surface 4, and the light distribution unevenness of the illumination light becomes significant at the imaging surface 4.

The light diffusion surface 11a then must be formed on the curvature surface of the illumination lens 11. The light diffusion surface 11a diffuses the exit light from the exit end face of the optical fiber bundle 33b when passing therethrough. That is, if the light diffusion surface 11a is not formed on the illumination lens 11, the light rays radiated as in L1 to L4 are passed through the light diffusion surface 11a, and projected onto the imaging surface 4 as L1', L2', L3', and L4', thereby resolving light distribution unevenness.

Generally, grinding and polishing process, and press process are methods of forming the illumination lens. In the grinding and polishing process, mirror finish is performed on the lens surface by changing the grind stone of large particles to the grind stone of fine particles in steps. The illumination lens 11 has the surface other than the light diffusion surface 11a performed with mirror finish process after the grinding and polishing process, so that the light diffusion surface 11a is formed to a sand-mesh shape through the grinding and polishing process.

Further, the illumination lens may be formed using the press process. In this case, since a molding die is also produced through grinding, the surface is not mirror finished, and is remained with a roughness of about a few micrometers to a few dozen micrometers. In this case, the lens formed with the light diffusion surface is produced with one step if such a die is used, whereby the process step is reduced and the prime cost of the lens is reduced. The surface of the die may be a micro lens shape, a diffuser shape, or a flannel lens.

Figure 5:
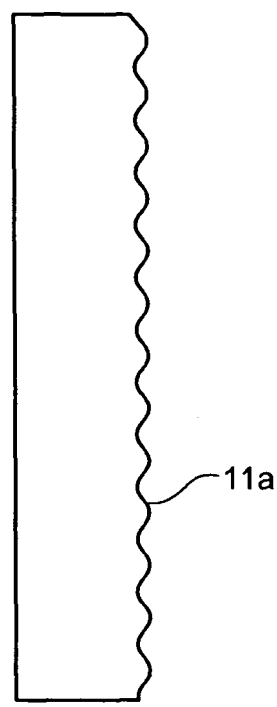
FIG. 5 is a partially enlarged front view of a light diffusion surface of the illumination lens of FIG. 4.

FIG. 5 shows a partially enlarged front view of the light diffusion surface 11a of the illumination lens 11 of FIG. 4, where the light diffusion surface 11a is generally performed with a process to have a sand-mesh shape through grinding and polishing, and thus the light diffusion surface 11a has a rough surface. In particular, the light diffusion surface formed with a grind stone of particles as large as #800 is very rough, and the optical transparency becomes about 30%.

The light diffusion surface formed with the grind stone of rough particles has a high light diffusion surface effect and is very effective in avoiding light distribution unevenness of the illumination light. However, such light diffusion surface generates a great amount of diffused reflection of light inside the lens or in the housing, whereby the light emitted from the optical fiber bundle 33b cannot be efficiently conveyed to the observation field, and the usage efficiency of the light degrades.

After the light diffusion surface 11a is performed with sand-mesh process and the light diffusion surface is formed, chemical surface treatment using hydrogen fluoride water is performed, so that a smooth light diffusion surface is formed as shown in FIG. 5. Thus, the light diffusion efficiency is reduced, and the mesh light distribution unevenness such as the above is reduced to a level that does not present any practical problem, while efficiently conveying the illumination light into the field of the physical surface, and resolving the problem of lack of amount of light around the field.

Further, the light diffusion surface 11a is arranged on at least one surface excluding the surface facing the body cavity, and thus dirt, dust and the like attached when observing or storing does not remain on the surface facing the body cavity of the illumination lens 11 after sterilization and cleaning, and thus hygienic problems do not arise.

Since the illumination lens 11 is configured with only one convex lens, the entire length and the outer shape of the optical system are miniaturized while maintaining wide light distribution. Thus, the outer diameter D of the distal end portion 10 of the endoscope insertion unit 3 is formed small compared to when the illumination optical system is configured by a plurality of illumination lenses.

Figure 6:
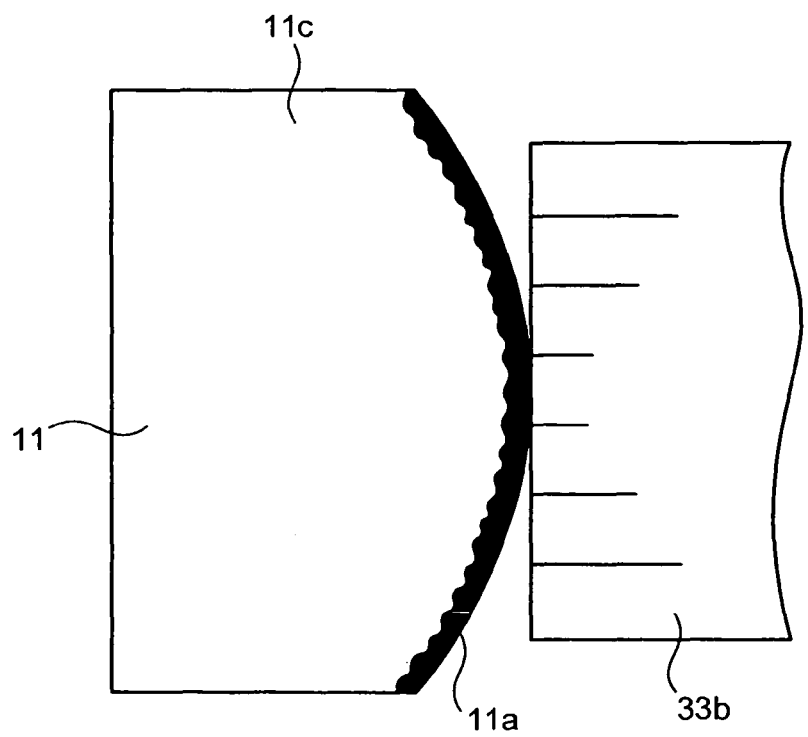
FIG. 6 is a partially enlarged front view of a side surface of the illumination lens of FIG. 4 performed with mirror surface process.

Further, the illumination lens 11 may have the side surface 11c formed into a mirror surface, as shown in FIG. 6. Thus, the light beam reflected diffusively by the light diffusing surface 11a illuminates the field of view of the imaging surface 4, and the illumination light from the exit end surface of the optical fiber bundle 33b can be efficiently used.

The air and water feeding nozzle 25 is made of metal for example, and an opening 25a is provided at the distal end side of the air and water feeding nozzle 25. The opening 25a is arranged so that water or air exhausted from the air and water feeding nozzle 25 is exhausted in a direction parallel to the plane orthogonal to the optical axis of the imaging unit 32 and in a direction passing through the surface of the objective lens 32a and the surface of the illumination lens 11.

The air and water feeding nozzle 25 is formed so as to project from the end surface 21 of the distal end portion 10 at a position not within the range of the viewing angle of the objective lens 32a.

Thus, the shape of the end surface 21 of the distal end portion 10 formed by the respective end surfaces of the cap 31a, the illumination lens 11, the objective lens 32a, and the air and water feeding nozzle 25 is a parabola having a slope.

The proximal end side of the air and water feeding nozzle 25 has a pipe shape, and is connected to a water feeding tube 25c by way of a connecting pipe 25b. Thus, a water feeding channel is formed by the connecting pipe 25b and the water feeding tube 25c. The water feeding tube 25c is fixed to the connecting pipe 25b by means of a reel 25d.

The proximal end of the distal end rigid portion 31 is fixed to one part of a curved distal end coma 35. The distal end side of the distal end rigid portion 31 and the curved distal end coma 35 are covered by a cover tube 36. The cover tube 36 is fixed to the distal end rigid portion 31 with the reel 37.

Thus, in the endoscope shown in the first embodiment of the present invention, the illumination lens 11 is configured with one convex lens formed with the light diffusion surface 11a on the curvature surface contacting the exit end face of the optical fiber bundle 33b and performed with light diffusion process.

The light diffusion surface 11a of the illumination lens 11 performed with the light diffusion process is performed with chemical surface treatment using hydrogen fluoride water after being subjected to the grinding and polishing process to be formed to a smooth light diffusion surface, and thus the illumination lens 11 reduces the light distribution unevenness to a level that does not present practical problems, and thoroughly guides the illumination to the field of the imaging surface efficiently and uniformly.

Since the illumination lens 11 is configured by only one convex lens, the entire length and the outer appearance of the optical system can be miniaturized while maintaining wide light distribution, and thus the outer diameter L of the distal end portion 10 of the endoscope insertion unit 3 can be formed small compared to when the illumination optical system is configured with a plurality of illumination lenses. Further, the production cost is reduced and assembling ability is enhanced since only one illumination lens is. arranged.

Thus, an endoscope that illuminates the observing range of wide angle of the observation optical system with sufficient brightness and light distribution without increasing the outer diameter, of the distal end portion of the endoscope insertion unit is provided.

One part of the optical fiber bundle 33b is arranged in the distal end rigid portion 31 so that the boundary of the rigid portion 33h and the soft portion 33f of the optical fiber bundle 33b, that is, the back end of the rigid portion 33h is positioned on the proximal end side than the back end face of the distal end rigid portion 31 in the inserting axis direction.

Thus, the worker is able to grasp the rigid portion 33h and insert the optical fiber bundle 33b to the distal end rigid portion 31, which pushing force is reliably conveyed to the distal end portion of the optical fiber bundle 33b thereby enhancing the assembling ability.

In the present embodiment, the illumination lens 11 is given by way of example and explained as the illumination lens, but is not limited thereto, and effects similar to the embodiment of the present invention are obviously obtained even when the illumination lens 12 or the illumination lens 13 is used.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
    an insertion unit;
    an observation optical system arranged at an end surface of the insertion unit in an inserting axis direction and having a wide viewing angle for observing a body cavity;
    at least one illumination lens arranged on an axis slanted with respect to the inserting axis direction of the insertion unit and used when illuminating the body cavity;
    an optical fiber bundle connected to a back surface of the illumination lens and including a rigid-portion connected to the back surface of the illumination lens and a soft portion connected to the rigid portion;
    a rigid part arranged in the insertion unit for holding the optical fiber bundle; and
    a fixing member which fixes the optical fiber bundle to the rigid part;
    wherein the illumination lens is subjected to light diffusion process, the rigid portion protrudes from a back end face of the rigid part, and the rigid portion is bent at a position between the back end face of the rigid part and the fixing member.

2. The endoscope according to claim 1, wherein the rigid portion of the optical fiber bundle is configured by bonding a plurality of optical fibers with an adhesive.

3. The endoscope according to claim 1, wherein the illumination lens is configured with one convex lens.

4. The endoscope according to claim 1, wherein the illumination lens has a light diffusion surface formed on at least one surface except for a surface facing an observed region of the body cavity.

5. The endoscope according to claim 4, wherein the light diffusion surface is formed on a curvature surface of the illumination lens.

6. The endoscope according to claim 4, wherein the light diffusion surface is formed through a grinding and polishing process.

7. The endoscope according to claim 4, wherein the light diffusion surface is formed through surface treatment using hydrogen fluoride water after a grinding and polishing process.

8. The endoscope according to claim 4, wherein the light diffusion surface is formed through a press process.

9. The endoscope according to claim 1, wherein the illumination lens has a side surface subjected to a mirror surface process 10. The endoscope according to claim 1, wherein three illumination optical systems are provided.

* * * * *